(12) United States Patent
Webb (10) Patent No.: US 8,231,033 B2
(45) Date of Patent: Jul. 31, 2012

(54) DISINFECTANT CAP FOR STERILE LIQUID DISPENSER

(75) Inventor: Garth T. Webb, Surrey (CA)

(73) Assignee: 0736413 B.C. Ltd., Surrey (CA)

( * ) Notice: Subject to any disclaimer, the term of this patent is extended or adjusted under 35 U.S.C. 154(b) by 528 days.

(21) Appl. No.: 12/530,859

(22) PCT Filed: Mar. 13, 2008

(86) PCT No.: PCT/CA2008/000503
§ 371 (c)(1),
(2), (4) Date: Oct. 20, 2009

(87) PCT Pub. No.: WO2008/110014
PCT Pub. Date: Sep. 18, 2008

(65) Prior Publication Data
US 2010/0044395 A1    Feb. 25, 2010

Related U.S. Application Data

(60) Provisional application No. 60/894,662, filed on Mar. 13, 2007.

(51) Int. Cl.
*B65D 47/00* (2006.01)
(52) U.S. Cl. ......... 222/562; 222/148; 222/494; 604/263
(58) Field of Classification Search ............... 222/562, 222/386.5, 389, 394, 420–422, 494, 402.1, 222/148–149; 604/197–199, 192, 263
See application file for complete search history.

(56) References Cited

U.S. PATENT DOCUMENTS 1,115,561 A    11/1914 Northey
(Continued)

FOREIGN PATENT DOCUMENTS

FR    2804846    8/2001
(Continued)

OTHER PUBLICATIONS

International Search Report completed on May 7, 2008 in respect of Patent Cooperation Treaty Application No. PCT/CA2008/000503 (Publ. No. WO 2008/110014).

(Continued)

*Primary Examiner* — Frederick C. Nicolas
(74) *Attorney, Agent, or Firm* — Bruce M. Green; Oyen Wiggs Green & Mutala LLP (57) ABSTRACT

A disinfectant cap for sterile liquid dispensers is disclosed. The cap includes a biocide-containing reservoir separated from the hollow interior of the cap by a rigid partition having an aperture therein for receiving the outlet port of the dispensing end of the dispenser, the cap being configured such that when in a closed configuration, the outlet port of the dispensing end extends through the aperture into the biocide-containing reservoir and the rigid partition is configured such that when the cap is removed from the dispensing end the biocide is retained in the reservoir. This may be achieved by selecting the size of the aperture such that when the cap is removed from the dispensing end the biocide is retained in the reservoir by surface tension. Or the partition may be provided with a hinged flap which seals the aperture when the cap is removed from the dispensing end and which is moved away from the aperture when the outlet port extends through the aperture.

14 Claims, 7 Drawing Sheets

U.S. PATENT DOCUMENTS

| | | | |
|---|---|---|---|
| 3,149,758 A | | 9/1964 | Bush et al. |
| 3,951,798 A | * | 4/1976 | Haldopoulos ................ 210/452 |
| 4,392,859 A | * | 7/1983 | Dent ............................ 604/198 |
| 4,463,880 A | | 8/1984 | Kramer et al. |
| 4,507,118 A | * | 3/1985 | Dent ............................ 604/198 |
| 4,533,068 A | | 8/1985 | Meierhoefer |
| 4,695,274 A | * | 9/1987 | Fox .............................. 604/198 |
| 4,938,389 A | | 7/1990 | Rossi et al. |
| 5,014,869 A | | 5/1991 | Hammond |
| 5,080,800 A | | 1/1992 | Heyl et al. |
| 5,105,993 A | | 4/1992 | La Haye et al. |
| 5,154,325 A | | 10/1992 | Ryder et al. |
| 5,370,313 A | | 12/1994 | Beard |
| 5,427,234 A | * | 6/1995 | Upchurch ..................... 206/210 |
| 5,433,343 A | | 7/1995 | Meshberg |
| 5,507,417 A | | 4/1996 | Webb |
| 5,516,006 A | | 5/1996 | Meshberg |
| 5,605,257 A | | 2/1997 | Beard |
| 5,611,464 A | | 3/1997 | Tsao et al. |
| 5,894,015 A | * | 4/1999 | Rechtin ........................ 422/301 |
| 5,992,701 A | | 11/1999 | Bougamont et al. |
| 6,000,580 A | * | 12/1999 | Nilson .......................... 222/108 |
| 6,095,376 A | * | 8/2000 | Hennemann et al. ......... 222/190 |
| 6,116,468 A | | 9/2000 | Nilson |
| 6,171,293 B1 | * | 1/2001 | Rowley et al. ................ 604/403 |
| 6,745,763 B2 | | 6/2004 | Webb |
| 6,824,015 B1 | | 11/2004 | Ammann |
| 7,186,045 B2 | | 3/2007 | Gueret |
| 2001/0031168 A1 | | 10/2001 | Gueret |
| 2006/0011654 A1 | | 1/2006 | Webb |
| 2006/0180613 A1 | | 8/2006 | Manesis |

FOREIGN PATENT DOCUMENTS

| | | |
|---|---|---|
| JP | 11-000378 | 1/1999 |
| JP | 2002-541034 | 12/2002 |
| WO | 93/24164 A1 | 12/1993 |
| WO | 00/61454 A1 | 10/2000 |

OTHER PUBLICATIONS

International Search Report completed on Oct. 7, 2005 in respect of Patent Cooperation Treaty Application No. PCT/CA2005/001094 (Publ. No. WO 2006/007690).

English translation of Abstract for FR 2804846 A1 published Aug. 17, 2001.

Patent Abstracts of Japan for JP 11-000378 published Jan. 6, 1999 to Eisai Co Ltd. "Medicine Bottle Cap".

* cited by examiner

DISINFECTANT CAP FOR STERILE LIQUID DISPENSER

TECHNICAL FIELD

The invention relates to the field of dispensers for sterile liquids.

BACKGROUND

Various ophthalmic and medical applications require a hand-held dispenser of multiple doses of sterile liquids. Sterile saline is required by contact lens wearers for use as a rinse solution, for rinsing the lens prior to inserting the lens in the eye, and also for soaking the lens during the cleaning and disinfecting process. Dispensers have been designed to maintain such liquids in a sterile state for dispensing, such as disclosed in the present inventor's U.S. Pat. No. 5,507,417, which discloses a dispenser for sterile saline solution and U.S. Pat. No. 6,745,763 which discloses a vaporizing device for administering sterile medication. Similarly, dispensers of medicinal liquids for eye, ear and nose drops desirably keep such liquids sterile between uses to prevent bacterial growth. An example of such device is disclosed in U.S. Pat. No. 4,533,068 Meierhoefer, wherein a hydrophobic filter is used to sterilize the replacement air which enters the dispenser upon release of the squeezing pressure. Other devices use an anti-bacterial hydrophobic filter over the outlet port, or hydrophobic and hydrophilic filters in tandem, to maintain the liquid sterile. See U.S. Pat. No. 3,149,758 Bush et al.; U.S. Pat. No. 4,938,389 Rossi et al. and Kramer et al. U.S. Pat. No. 4,463,880.

Commonly such dispensers use a one-way valve or pump with a one-way valve to dispense the sterile liquid from a squeeze bottle or collapsible reservoir. A problem with existing devices is that after the sterile liquid is dispensed, some residue remains on the outlet port, or is drawn back into the outlet conduit, which can become contaminated with bacteria or the like and which will contaminate the next dose of the sterile liquid which is dispensed through the outlet port. There is therefore a need to avoid the foregoing problem with sterile liquid dispensers.

SUMMARY OF INVENTION

The present invention provides a disinfectant cap for sterile liquid dispensers. The invention provides a cap for a dispenser for sterile liquid having a hollow container for storing said sterile liquid and a dispensing end having an outlet port, the cap comprising a closed end and an open end, a hollow interior communicating with the open end and a biocide-containing reservoir separated from the hollow interior by a rigid partition having an aperture therein for receiving the outlet port of the dispensing end, the cap being configured such that when in a closed configuration, the outlet port of the dispensing end extends through the aperture into the biocide-containing reservoir and wherein the rigid partition is configured such that when the cap is removed from the dispensing end the biocide is retained in the reservoir. According to one aspect of the invention, the size of the aperture is selected such that when the cap is removed from the dispensing end the biocide is retained in the reservoir by surface tension. According to another aspect of the invention, the partition is provided with a hinged flap which seals the aperture when the cap is removed from the dispensing end and which is moved away from the aperture when the outlet port extends through the aperture. The invention also provides a sterile liquid dispenser incorporating the foregoing cap.

BRIEF DESCRIPTION OF DRAWINGS

In drawings which disclose a preferred embodiment of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

With reference to FIG. 5-8, a sterile liquid dispenser 10 comprises a hollow, rigid cylindrical container 20 which has hollow interior 11 containing sterile liquid 12 and pressurized gas 13. Dispenser 10 can be a pressurized dispenser of the type disclosed in the present inventor's international application number PCT/CA2006/001551 entitled "Pressurized Sterile Liquid Dispenser" which is pending and is incorporated herein by reference. Pressurized dispenser 10 has pressurized storage reservoir 11 for storing the sterile liquid 12, which is injected into the reservoir through bottom filling valve 15. Typically the container 20 will be constructed of a rigid molded plastic such as a polycarbonate. The container 20 may have a threads 17 adjacent neck 18 to which a cap 14 may be screwed in place. Alternatively cap 14 may be sized and constructed to provide a friction or snap fit over neck 18 of container 20. Dispenser 10 has a flexible nozzle 22 which is molded of a rubber such as used in syringes and is molded or welded integrally onto a rigid retainer ring 24 secured by glue or welding to neck 18 of container 20. Extending upwardly from neck 18 is hollow cylindrical element 25 which surrounds cylindrical chamber 26 and which connects at its upper end to solid conical plug 28. A cylindrical elastomeric valve 30 is seated against the lower surface of plug 28, at the upper end of chamber 26. At rest, valve 30 seals a passage 32 which communicates between chamber 26 and annular chamber 36 between the outer surface of plug 28 and the inner surface of nozzle 22 which extends over plug 28. A knob 38 can be pressed into contact with the outer surface of valve 30 and to open passage 32 when actuating surface 40 is pressed, thereby forcing knob 38 inwardly against valve 30.

Figures 7, 8:
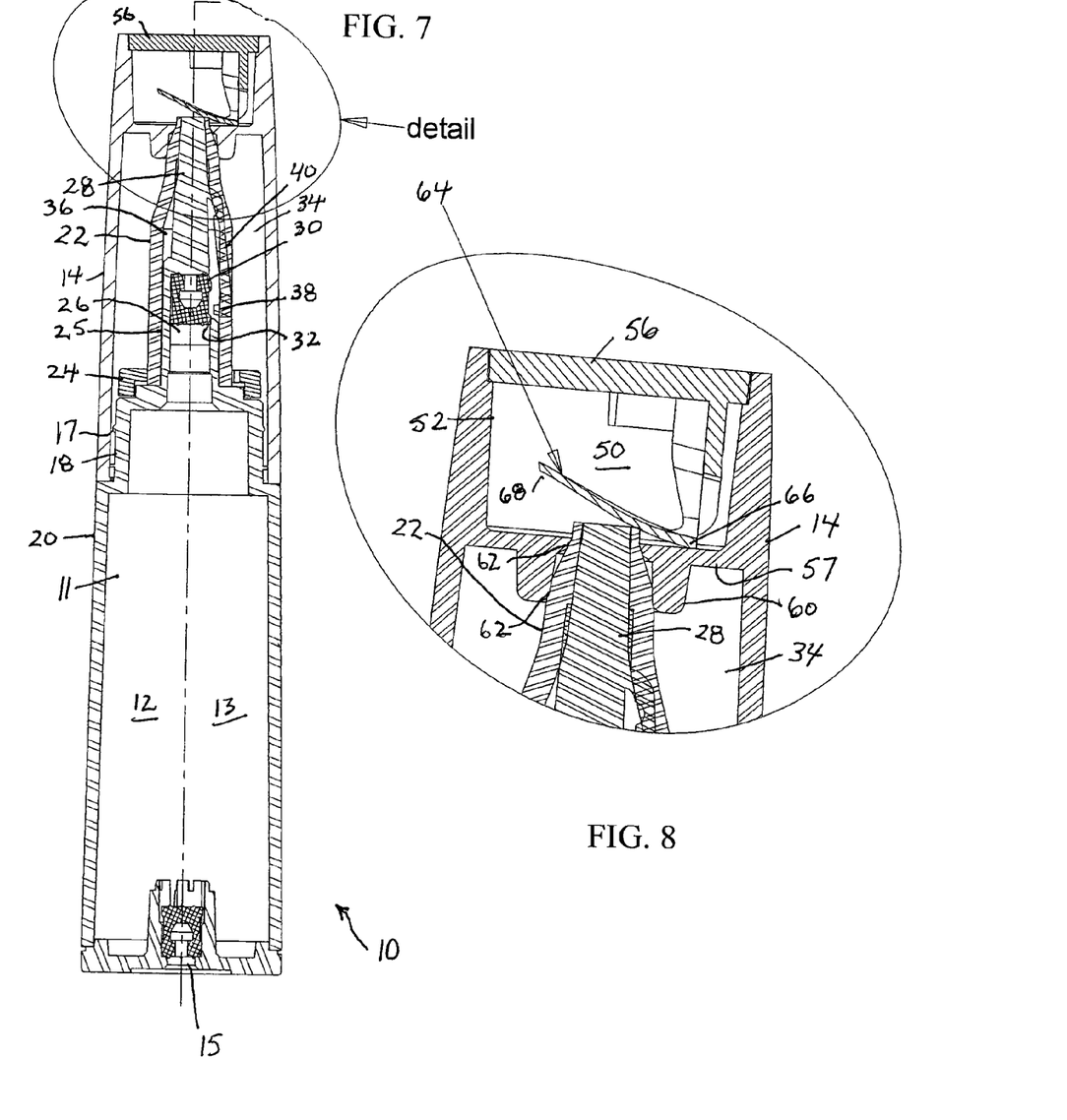
FIG. 7 is a vertical cross section of the first embodiment of the invention shown in FIG. 3 taken along line A-A of FIG. 6.
FIG. 8 is a detail of the section indicated in FIG. 7.

In operation, cap 14 is removed from container 20, which is then inverted. Actuating surface 40 is pressed, thereby opening passage 32. When passage 32 is opened, liquid under pressure from reservoir 12 is forced through passage 32 into chamber 36 and moves nozzle 22 away from plug 28 to form a liquid droplet at the end of nozzle 22. The size of passage 32, chamber 36 and the diameter and flexibility of nozzle 22 are selected so that droplets of liquid 12 of suitable size are formed within the selected time frame. Once the droplet releases, the actuator surface 40 is released. After dispensing the drops, cap 14 is replaced on container 20 with nozzle 22 received in the hollow interior 34 of cap 14.

Figure 1:
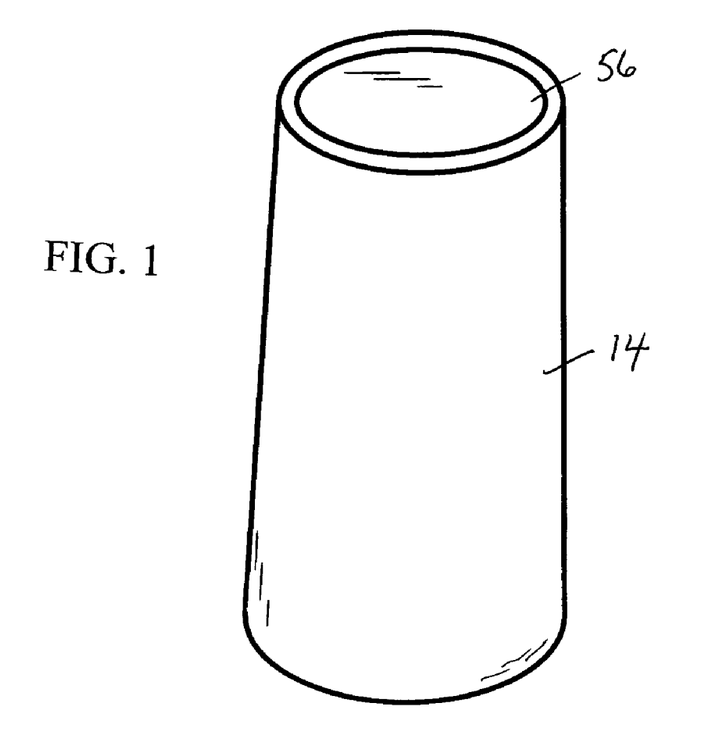
FIG. 1 is a perspective view of a disinfectant cap according to the invention.
Figure 2:
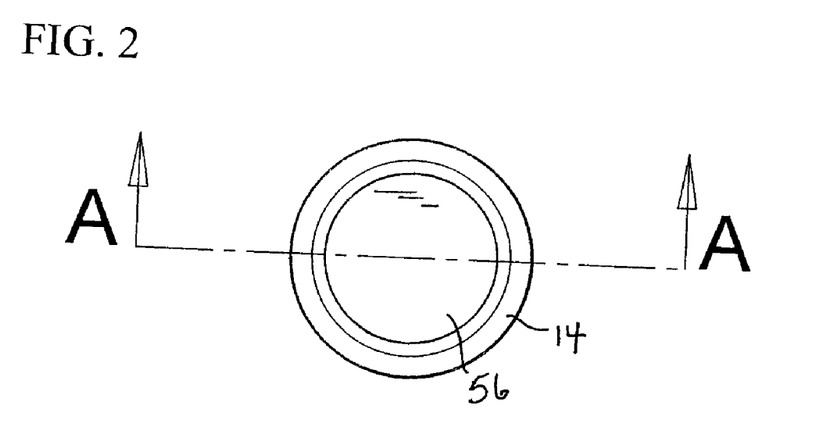
FIG. 2 is a top view of the disinfectant cap shown in FIG. 1.
Figure 3:
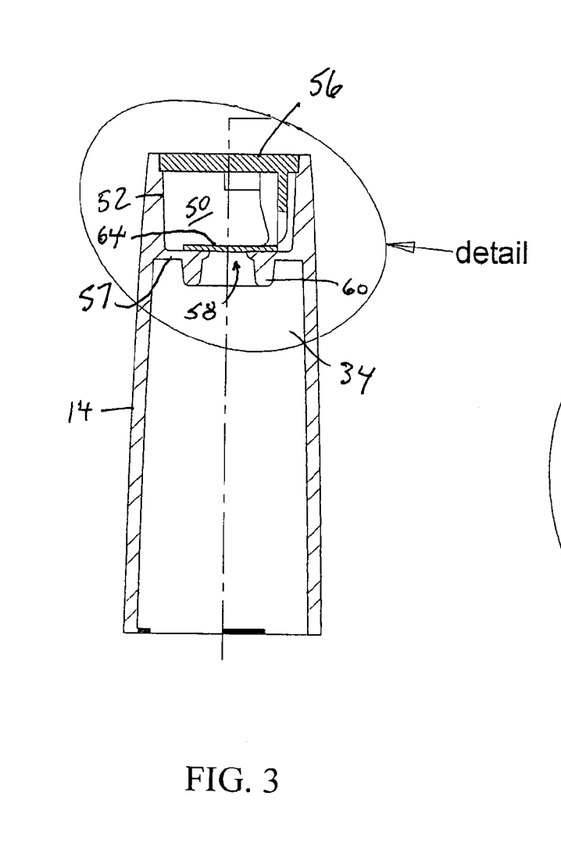
FIG. 3 is a vertical cross section of a first embodiment of the invention taken along line A-A of FIG. 2.
Figure 4:
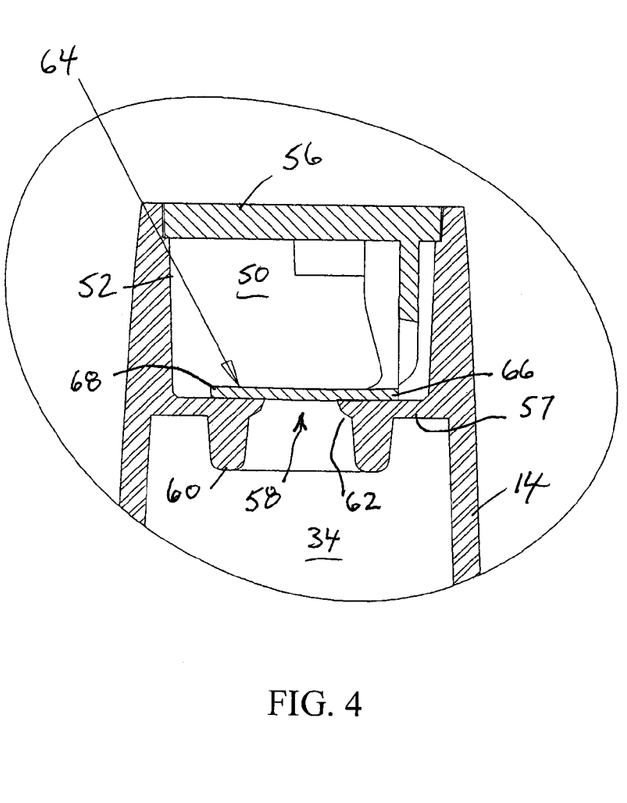
FIG. 4 is a detail of the section indicated in FIG. 3.
Figure 5:
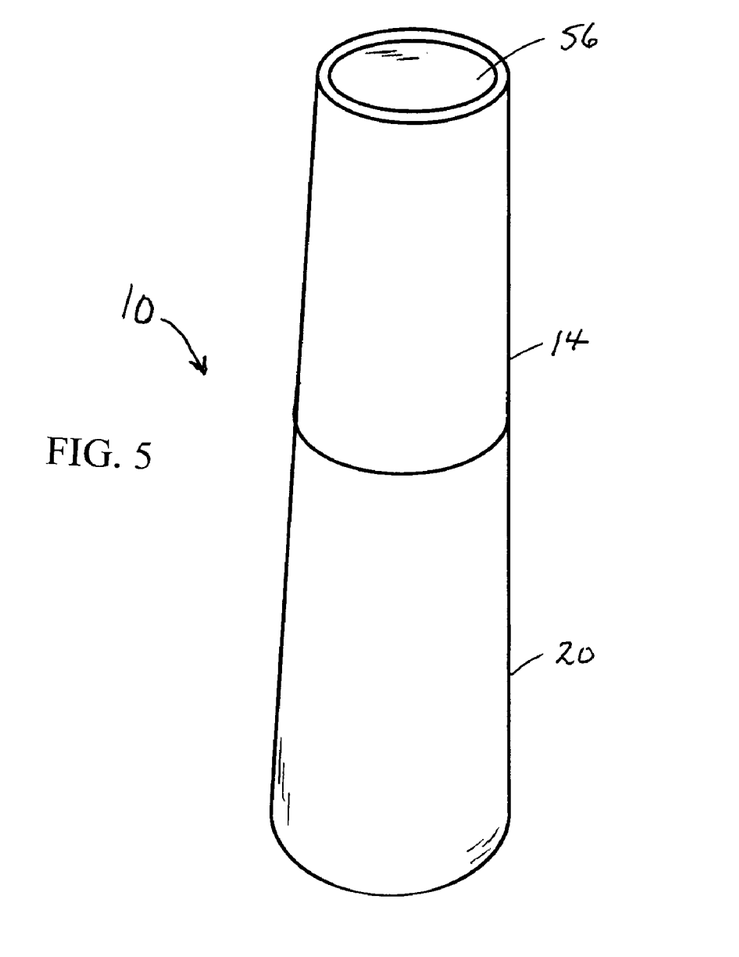
FIG. 5 is a perspective view of a disinfectant cap in place on a dispenser according to the invention.
Figure 6:
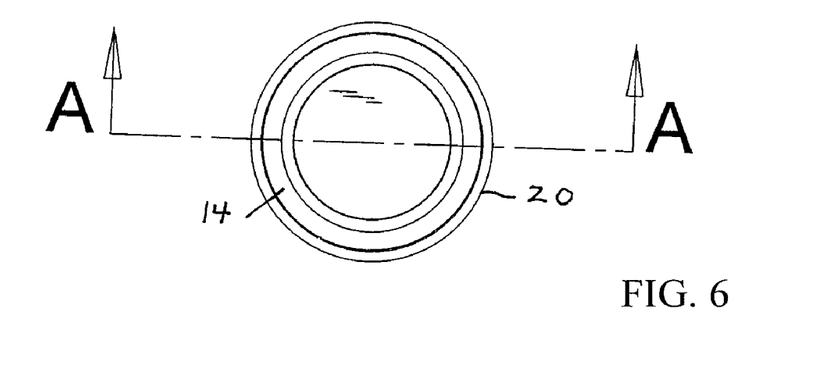
FIG. 6 is a top view of the disinfectant cap and dispenser shown in FIG. 5.

To preserve the sterility of sterile liquid 12 when the liquid is dispensed from nozzle 22, cap 14 is provided with a quantity of biocide 50 or other disinfectant, such as a gel or liquid, stored in hollow cylindrical chamber 52. A circular lid 56 is secured by welding or gluing to form the upper wall of chamber 52. Chamber 52 is separated from the hollow interior 34 of cap 14 by a wall 57 having a central opening 58. A circular flange 60 extends downwardly from wall 57 around central opening 58, and has tapered inner surfaces 62 which receives the end of nozzle 22 and allows only the tip of nozzle 22 to extend into chamber 52, as illustrated in FIG. 8. The size of central opening 58 and the relative configurations of the nozzle 22 and surface 62 flange 60 are such that when the cap 14 is replaced on container 20, the end of nozzle 22 can extend through opening 58 into chamber 52 but the sides of nozzle 22 tightly seal against surfaces 62, as shown in FIG. 8. As illustrated in FIG. 4, central opening 58 is sealed by a flexible hinged flap 64 when cap 14 is removed from the container 20. Flap 64 is made of a resilient rubber material or the like and forms a one-way valve sealing central opening 58. One end 66 of flap 64 is secured to the upper surface of wall 57 while the opposite end 68 of flap 64 is free to be raised upwardly into chamber 52 when contacted by nozzle 22.

Chamber 52 is partially filled with biocide 50 prior to use using a needle or other injector inserted through opening 58. Some air space is left in chamber 52 so that flap 64 can open when the nozzle 52 is inserted into opening 58.

When cap 14 is replaced over the dispensing nozzle 22, as shown in FIG. 8, the end of nozzle 22 extends through central opening 58 and is immersed in the biocide 50, thereby placing biocide in contact with the surface of the tip of nozzle 22. The end of nozzle 22 is thus sterilized during storage and prior to each dispensing of liquid. When cap 14 is removed from container 20, nozzle 22 is withdrawn from the central opening 58. As the tip of nozzle 22 is drawn downwardly in opening 58, the resiliency and flexibility of flap 64 is such that it slides across the face of the tip of nozzle 22 with a wiping or squeegee action, thereby wiping substantially all biocide from the tip of nozzle 22 as it is withdrawn and preventing any biocide from leaking through opening 58. Once nozzle 22 is withdrawn below the upper surface of wall 57, and end 68 of flap 64 rests against the upper surface of wall 57, opening 58 is then sealed by flap 64 to retain the biocide or other disinfectant within chamber 52.

Figure 9:
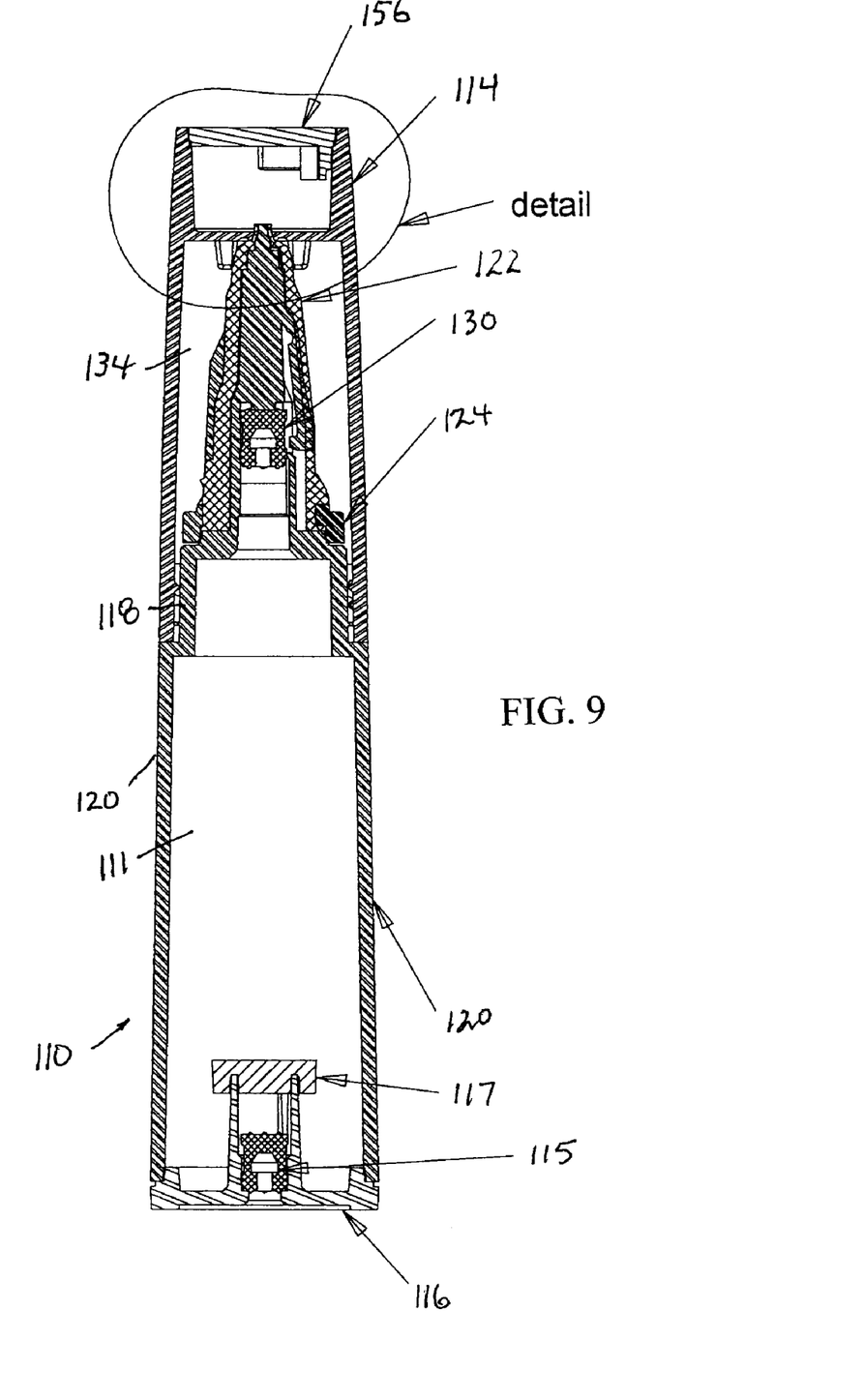
FIG. 9 is a vertical cross section of a second embodiment of the invention taken along line A-A of FIG. 6.
Figure 10:
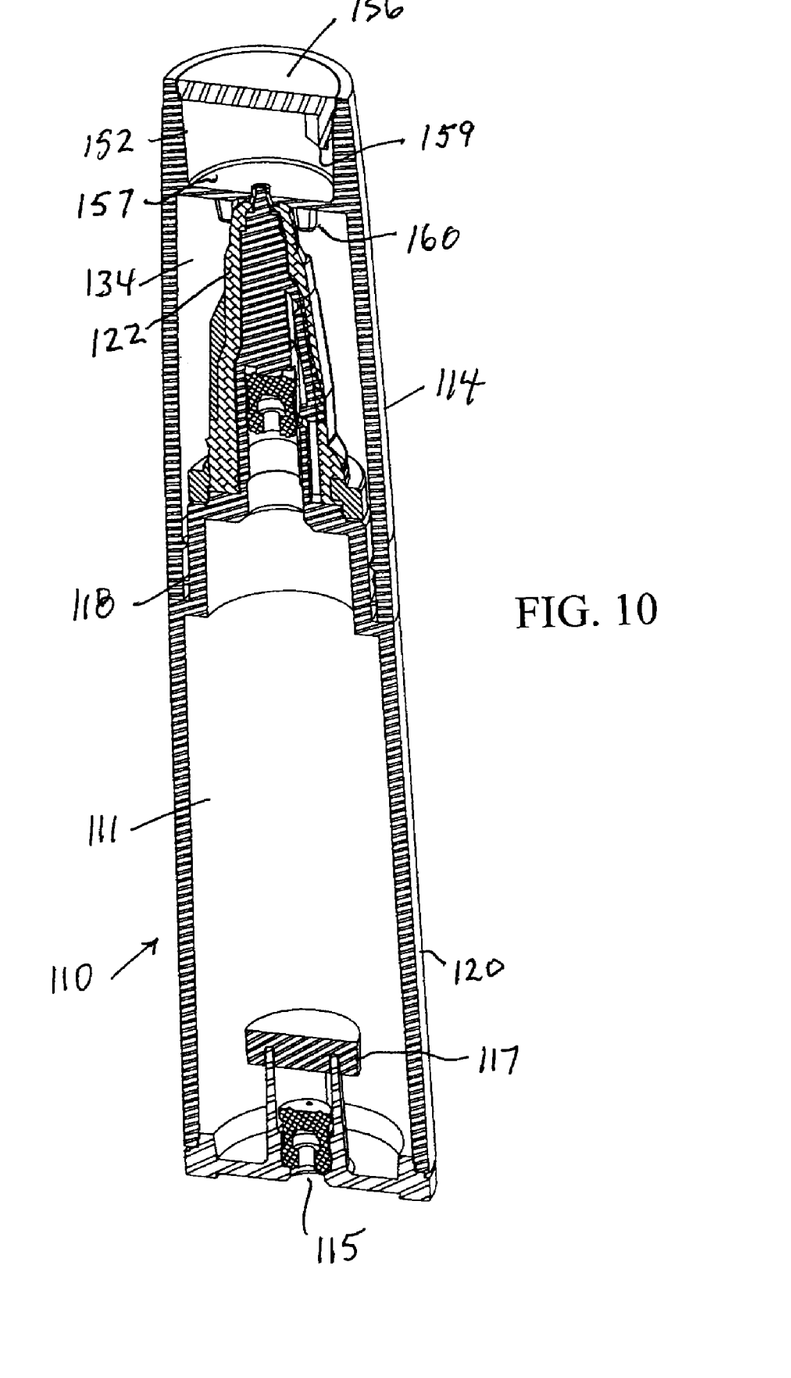
FIG. 10 is a vertical cross section of a second embodiment of the invention taken along line A-A of FIG. 6 and shown in perspective.
Figure 11:
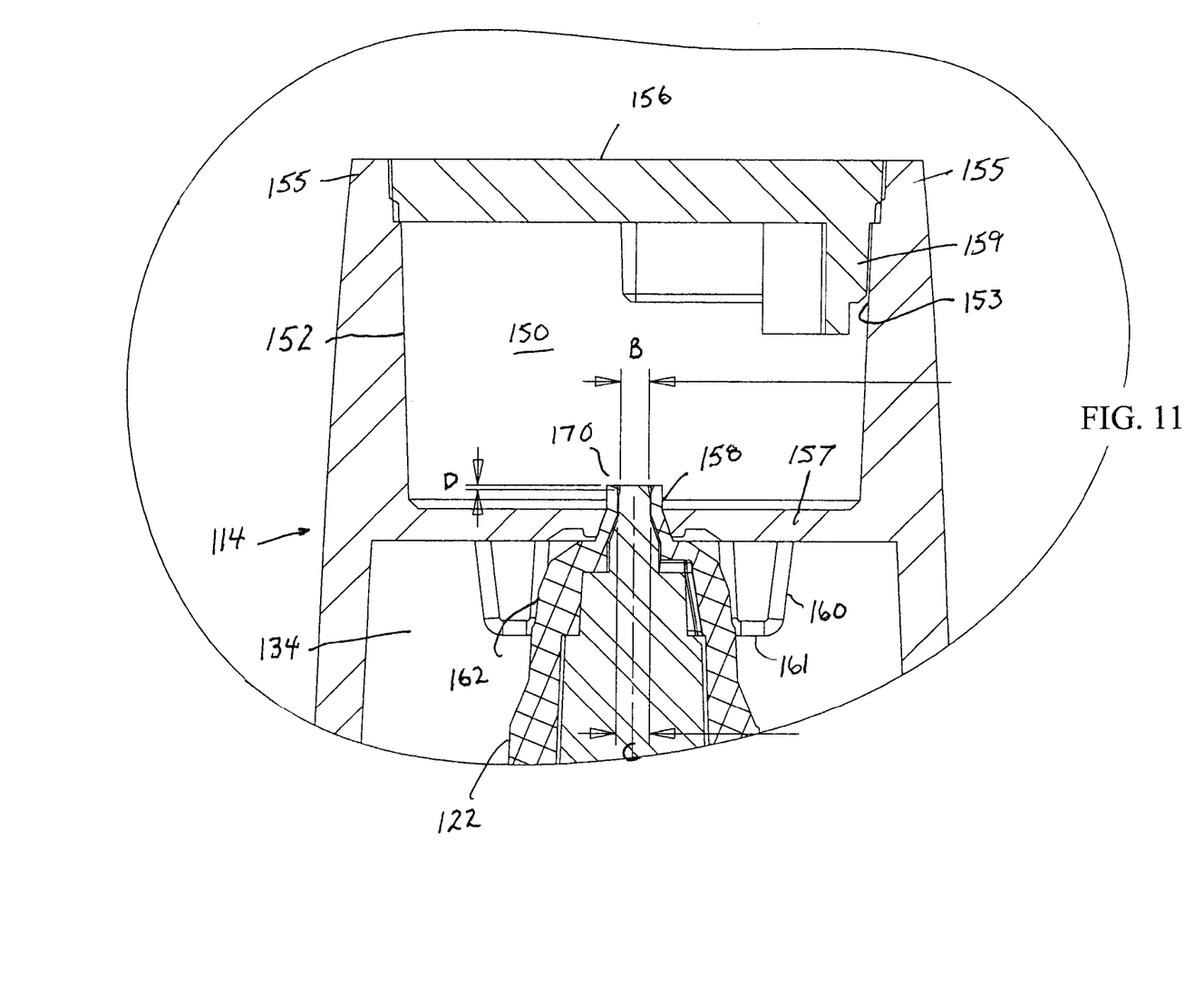
FIG. 11 is a detail of the section indicated in FIG. 9.

A second embodiment of the invention which does not require flap 68 is illustrated in FIG. 9-11. The sterile liquid dispenser 110 is of the same type as disclosed in FIG. 7 and comprises a hollow, rigid cylindrical container 120 which has a hollow interior 111 containing sterile liquid and pressurized gas. Pressurized dispenser 110 has a cap 114. The sterile liquid is injected into the interior 111 through bottom filling valve 115 which may be covered with a bottom cover secured at 116. The retainer for the filling valve is shown at 117. Typically the container 120 and cap 114 will be constructed of a rigid molded plastic such as a polypropylene or polycarbonate. Cap 114 may be screwed in place or may be sized and constructed to provide a friction or snap fit over neck 118 of container 120. Dispenser 110 has a flexible nozzle 122 which is molded of rubber and is molded or welded integrally onto a rigid retainer ring 24 secured by glue or welding to neck 118 of container 120. Elastomeric valve 130 functions as described above to dispense the sterile liquid after removing cap 114. After dispensing the liquid, cap 114 is replaced on container 120 with nozzle 122 received in the hollow interior 134 of cap 114.

To preserve the sterility of the sterile liquid when the liquid is dispensed from nozzle 122, cap 114 is provided with a quantity of biocide 150 or other disinfectant, such as a gel or liquid, stored in hollow cylindrical chamber 152. Hollow cylindrical chamber 152 may be manufactured by ultrasonically welding or gluing a circular lid 156 to the inner surface of wall 155 of cap 114. A stronger bond between cap 114 and lid 156 can be achieved by providing a downwardly extending curved element 159 which is secured by welding to the inner surface 153 of the upper wall of chamber 152. Chamber 152 is separated from the hollow interior 134 of cap 114 by a rigid wall 157 having a central opening or aperture 158. Annular ridge or shoulder 160, 161 extends downwardly from wall 157 around central opening 158, and has a tapered inner surface 162 which receives the end of nozzle 122 and allows only the tip of nozzle 122 to extend into chamber 152, as illustrated in FIG. 11. There may be breaks in the continuity of ridge 160 to release pressure when the tip of nozzle 122 is being guided into opening 158. The size of central opening 158 and the relative configurations of the nozzle 122 and surface 162 of rib 160 are such that when the cap 114 is replaced on container 120, the end of nozzle 122 can extend through opening 158 into chamber 152, as shown in FIG. 11. Preferably the tip 170 of nozzle 122 tapers slightly inwardly as shown in FIG. 11 where, for example diameter B is slightly less than diameter C. In this way the lower part of 170 contacts the inner edge of opening 158. Also a narrow rubber collar (not shown) may be provided around the end of tip 170, having width D, to compress the end of the tip and help keep liquid trapped within the end of tip 170.

Chamber 152 is wholly or partially filled with biocide 150 prior to use using a needle or other injector inserted through opening 158. As will be apparent to those skilled in the art, various types of liquid, semi-liquid or gel biocides or disinfectants are suitable for this purpose. One class of suitable liquid disinfectants are non-toxic polymer disinfectants such as benzylkonium chloride in aqueous solution. A second class of suitable liquid disinfectants are salts of sorbate such as sorbic acid in aqueous solution. A third class are aromatic alcohols such as benzyl alcohol and a fourth is colloidal silver. Disinfectant gels such as peroxygel are also suitable. As described below, the nature of the biocide or disinfectant in terms of viscosity, density, surface tension and the like, as well as the diameter of the tip 170 of nozzle 122 will determine the possible ranges of diameters of the central opening 158.

When cap 114 is replaced over the dispensing nozzle 122, as shown in FIG. 9-11, the end of nozzle 122 extends through central opening 158 and is immersed in the biocide 150, thereby placing biocide in contact with the surface of the tip of nozzle 122. The end of nozzle 122 is thus sterilized during storage and prior to each dispensing of liquid. When cap 114 is removed from container 120, nozzle 122 is withdrawn from the central opening 158. In this second embodiment the biocide or other disinfectant is retained within chamber 152 and prevented from leaking out opening 158 by surface tension. The surface tension created by the liquid is sufficient to prevent it from flowing out opening 158. To achieve this function, the diameter of opening 158 must be within a suitable range, which will depend on the nature of the biocide or disinfectant. Whereas the preferred range for the diameter of opening 58 in the first embodiment is from 0.1 mm to 1 cm., the preferred range for the diameter of opening 158 in the second embodiment is from 0.2 mm to 5 mm depending on the type of biocide, with a preferred diameter of about 2.5 mm for liquid biocides.

As will be apparent to those skilled in the art in the light of the foregoing disclosure, many alterations and modifications are possible in the practice of this invention without departing from the spirit or scope thereof.

What is claimed is:

1. A cap for a dispenser for sterile liquid having a hollow container for storing said sterile liquid and a dispensing end having an outlet port, said cap comprising a closed end and an open end, a hollow interior communicating with said open end and a biocide-containing reservoir separated from said hollow interior by a rigid partition having an aperture therein for receiving said outlet port of said dispensing end, said cap being configured such that when in a closed configuration, said outlet port of said dispensing end extends through said aperture into said biocide-containing reservoir and wherein said rigid partition is configured such that when said cap is removed from said dispensing end said biocide is retained in said reservoir.

2. The cap of claim 1 wherein the size of said aperture is selected such that when said cap is removed from said dispensing end said biocide is retained in said reservoir by surface tension.

3. The cap of claim 1 wherein said partition is provided with a hinged flap which seals said aperture when said cap is removed from said dispensing end and which is moved away from said aperture when said outlet port extends through said aperture.

4. The cap of claim 1 wherein said biocide-containing reservoir comprises a liquid biocide.

5. The cap of claim 1 wherein said biocide-containing reservoir comprises a semi-liquid biocide.

6. The cap of claim 1 wherein said biocide-containing reservoir comprises a gel biocide.

7. The cap of claim 2 wherein said size of said aperture is from 0.2 mm to 5 mm in diameter.

8. A dispenser for sterile liquid comprising a hollow container for storing said sterile liquid, a dispensing end having an outlet port, and a cap, said cap comprising a closed end and an open end, a hollow interior communicating with said open end and a biocide-containing reservoir separated from said hollow interior by a rigid partition having an aperture therein for receiving said outlet port of said dispensing end, said cap being configured such that when in a closed configuration, said outlet port of said dispensing end extends through said aperture into said biocide-containing reservoir and wherein said rigid partition is configured such that when said cap is removed from said dispensing end said biocide is retained in said reservoir.

9. The dispenser of claim 8 wherein the size of said aperture is selected such that when said cap is removed from said dispensing end said biocide is retained in said reservoir by surface tension.

10. The dispenser of claim 8 wherein said partition is provided with a hinged flap which seals said aperture when said cap is removed from said dispensing end and which is moved away from said aperture when said outlet port extends through said aperture.

11. The dispenser of claim 8 wherein said biocide-containing reservoir comprises a liquid biocide.

12. The dispenser of claim 8 wherein said biocide-containing reservoir comprises a semi-liquid biocide.

13. The dispenser of claim 8 wherein said biocide-containing reservoir comprises a gel biocide.

14. The dispenser of claim 9 wherein said size of said aperture is from 0.2 mm to 5 mm in diameter.

* * * * *